United States Patent [19]

Bourgeois

[11] Patent Number: 4,498,478

[45] Date of Patent: Feb. 12, 1985

[54] APPARATUS FOR REDUCING POLARIZATION POTENTIALS IN A PACEMAKER

[75] Inventor: Ivan M. Bourgeois, Thimister, Belgium

[73] Assignee: Medtronic, Inc., Minneapolis, Minn.

[21] Appl. No.: 417,256

[22] Filed: Sep. 13, 1982

[51] Int. Cl.³ ............................................. A61N 1/36
[52] U.S. Cl. ............................................. 128/419 PG
[58] Field of Search .................. 128/419 PG, 419 PT

[56] References Cited

U.S. PATENT DOCUMENTS

| | | | |
|---|---|---|---|
| 3,759,266 | 9/1973 | Lee .............................. | 128/419 PG |
| 4,056,105 | 11/1977 | Ravas ........................... | 128/419 PG |
| 4,114,627 | 9/1978 | Lewyn et al. ................. | 128/419 PG |
| 4,343,311 | 8/1982 | Markowitz ................... | 128/419 PG |
| 4,378,020 | 3/1983 | Nappholz et al. ............ | 128/419 PG |

FOREIGN PATENT DOCUMENTS

| | | |
|---|---|---|
| 2520729 | 11/1975 | Fed. Rep. of Germany ...... 128/419 PG |
| 2619001 | 11/1977 | Fed. Rep. of Germany ...... 128/419 PG |

OTHER PUBLICATIONS

Varriale, M.D., Philip and Naclerio, M.D. Emil A., *Cardiac Pacing*, Lea and Febiger, 1979, pp. 298, 299.

Primary Examiner—William E. Kamm
Attorney, Agent, or Firm—Joseph F. Breimayer; John L. Rooney; Robert C. Beck

[57] ABSTRACT

A method and apparatus embodied in a pacemaker for attenuating polarization currents or voltages at the output terminals of the pulse generator. A heart pacemaker typically possesses a source of supply voltage, an output capacitor, an output terminal adapted to be coupled to heart tissue. A voltage source is coupled to the output capacitor during a first time interval for charging the output capacitor to a certain voltage. The output capacitor is coupled to the output terminals during a second time interval to discharge its voltage into the heart tissue. A resistor is coupled across the output terminals for providing a current path for the discharging and recharging of the effective capacitance of the stimulated heart tissue. The resistor may be coupled across the output terminals only during the first time interval and not during the discharge of the output capacitor.

16 Claims, 7 Drawing Figures

APPARATUS FOR REDUCING POLARIZATION POTENTIALS IN A PACEMAKER

BACKGROUND OF THE INVENTION

1. Technical Field of the Invention

This invention pertains generally to the field of electrical heart pacemakers, including atrial and ventricular heart pacemakers, and more specifically to a method and apparatus for attenuating polarization voltages at the heart tissue-electrode surface interface following the delivery of a pacing stimulus to the heart tissue.

2. Description of the Prior Art

Heart pacemakers are designed for use on patients whose heart exhibits a failure in the conduction system which manifests itself in many ways, including slow or non-existent heart rates or disassociation of the synchronous contraction of the atrium and the ventricle of the heart. For example, atrial synchronous pacemakers are designed for use on patients whose hearts have normal atrial self-pacing but, due to a defect in the conduction from the atrium to the ventricle, the ventricles fail to beat or keep pace with the atrial depolarization. Irrespective of whichever pacemaker system is actually employed to restore the rhythm of the heart, all operate in a fashion to stimulate excitable heart tissue cells adjacent to the electrode of the pacing lead employed with the pacemaker.

Each heart cell contains positive and negative charges due to the selective absorption of certain ions, such as potassium and sodium through the cell membrane. When the cell is at rest, the inside of the cell is negatively charged with respect to the outside. A stimulus of any kind applied to the cell membrane causes the permeability of the cell membrane to change and allows the ingress of positive charge ions. The resulting dissipation of the negative charges constitutes the "depolarization" of the cell. Simultaneously, the cell contracts causing (in conjunction with the contraction of adjoining cells) the heart muscle to contract. Thus, the stimulation of the heart muscle affects both the contraction of the heart and the depolarization of the once-polarized myocardial cells which make up the muscle.

Following depolarization and contraction of a heart cell, the "repolarization" or recovery of the cell, so that it is ready to receive the next stimulus, commences. During the repolarization time interval, the cell membrane begins to pump out the positive-charged ions that have entered following the application of the stimulus, that is, during the depolarization of the cell. As these positive charges leave, the inside of the cell membrane starts to become negative again and the cell relaxes. In this state, a potential difference builds up, and the cell is said to be repolarized.

The individual myocardial cells are arranged to form muscle sheets which, in gross, constitute the heart itself. The depolarization and repolarization signals of the ventricle, viewed by an electrocardiogram (ECG) are referred to as the QRS wave and the T wave, respectively. The sequence of depolarization that manifests itself in a contraction of the heart muscle and repolarization which manifests itself in the relaxation and filling of the interior chambers of the heart with blood is accomplished through a system of specialized muscle tissue that functions like a nerve network. This system provides electrical stimulating pulses, at a rate which is appropriate for the body's needs. The system then conducts these impulses rapidly to all the muscle fibers of the ventricles, ensuring coordinated, synchronized pumping. It is when this system fails, or is overriden by abnormal mechanisms, that an electronic pacemaker may be needed to generate the triggering stimulus and maintain proper heart rate and synchronization of the filling and contraction of the atrial and ventricular chambers of the heart.

A further phenomena, "polarization voltage" manifests itself at the electrode-tissue interface upon delivery of a pacemaker stimulation pulse to the tissue.

The polarization voltage is an electrochemical potential, represented by the accumulation of a layer of opposite charges at the electrode-tissue phase boundary during the stimulation pulse. Polarization voltage rises to a peak during the stimulus pulse and then decays by defusion into the tissues, usually disappearing within 100 to 500 msec, before the subsequent pacemaker pulse. Polarization effect is inversely realted to the electrode surface area and directly related to the pulse width.

A pacemaker of relatively short refractory period may sense a prolonged voltage decay waveform or pulse after potential and induce recycling from its own stimulus discharge. The emergence of a prolonged escape interval that is recycled by the pacemaker polarization effect and includes one refractory period and one automatic interval is designated "double reset." A constant regular prolongation of the escape interval that includes the pacemaker automatic interval and its refractory period can be related to sensing of an inapparent signal that occurs immediately outside the refractory period of the pacemaker; this ECG finding should arouse suspicion of oversensing secondary to T wave voltage and/or pacemaker polarization voltage.

This description of the polarization voltage appears in the textbook *Cardiac Pacing—A Concise Guide to Clinical Practice,* Phillip Verriale, M.D. and Emil Naclerio, M.D., published in 1979 by Lee and Febiger, page 299.

These authors further state that the oversensing may be due to P wave sensing at the ventricular lead, if the lead is poorly positioned. In any case, in a classic single-chamber pacemaker, oversensing may be caused by the effects of the residual polarization voltage and/or the T wave and/or the P wave occuring at the end of the sense amplifier refractory interval. These authors conclude that "Oversensing due to pacemaker polarization effect, although rare, may continue to be a problem with pulse generators that offer a relatively short refractory period and longer stimulus pulse width of 1.5 msec or more, when used with an electrode of small surface area." (page 299).

This background information is useful in understanding the nature of the problem which had led to the method and apparatus of the present invention. The operation of a heart muscle itself, that is the polarization of the cell membrane, the depolarization in response to a stimulus and the subsequent repolarization suggests that the electrode-tissue interface operates in a fashion similar to a capacitive reactance. In reference to FIG. 1, the electrode-tissue interface can be represented through an electrical impedance which constitutes a series resistor $R_S$ in series electrically with the parallel combination of a Faraday resistor $R_F$ and a Helmholtz capacitor $C_H$. The resistor $R_S$ has a nominal value of about 10-200 ohms, the capacitor $C_H$ has a nominal value of about 5-50 microfarads, and the resistor $R_F$ has a nominal value of 2-100 kilo ohms. These values apply for the impedance measured in gross terms across the output terminals of the pulse generator. In the latter case the value of series resistor $R_S$ may reflect the lead and tissue resistance (about 100 ohms typically). These values vary with pacing stimuli.

Figure 2:
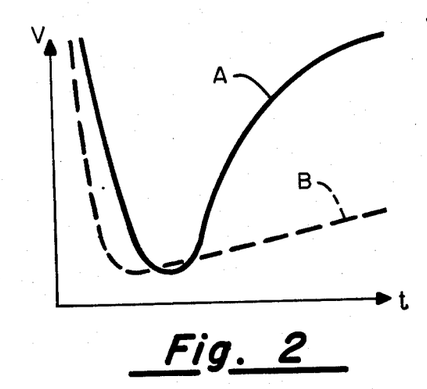
FIG. 2 is a waveform diagram depicting the polarization voltage after fast recharge of the output capacitor.

In the field of cardiac pacing, the depolarization and repolarization phenomena has affected the ability of the pacemaker sense amplifier to respond accurately and reliably to signals at its input terminal (which is typically connected to the output terminal of the pulse generator) during the repolarization time interval. Pacemaker sense amplifiers are commonly designed to respond to slew rates of the signal at the input terminals, and the repolarization voltage superimposed on the polarization voltage may present a high enough slew rate to create a false triggering problem known as T wave sensing. Certainly the slew rate of the polarization voltage waveform A, FIG. 2, presents a serious problem for a sensitive sense amplifier. In the past, typical pacemaker sense amplifier design has involved the employment of a relatively long refractory interval following the delivery of the stimulation pulse to correspond generally to the heart's own refractory interval, that is, the interval during which the myocardial cells will not react to reapplication of a further stimulus. This has meant that the sense amplifier output signals during the refractory interval have either been ignored or suppressed in past sense amplifier design. The prior art sense amplifier is, therefore, only made responsive to signals at the input terminals manifested after the lapse of the refractory period and the repolarization interval.

The more recent developments of atrial and ventricular pacemakers has made it desirable to be able, at the ventricular sense amplifier for example, to sense the presence or absence of a ventricular depolarization following an atrial stimulus. In addition, it has been considered desirable to be able to verify the capture of the heart by a pacing stimulus by sensing for an evoked depolarization shortly following the delivery of a pacing stimulus. The slew rate of the polarization voltage has in these instances complicated the design of such circuits.

A further complication to pacemaker sense amplifier design lies in the charge and recharge cycle of the pacemaker output capacitor. Typically, the stimulus delivered to the heart is generated by discharging an output capacitor coupled in the output terminals of the pulse generator which, in turn, are adapted to be coupled through a pacing lead to pacing electrodes and to the heart impedance depicted in FIG. 1. The discharge of the pacing capacitance into the capacitive reactance of the heart results in a complex voltage discharge curve at the input terminals of the sense amplifier (which is typically rendered inoperative during the discharge interval of the output capacitor). The recharge of the output capacitor takes place at the end of the discharge and can be roughly contemporaneous with the repolarization of the myocardial cells or shorter. Thus, the recharge of the output capacitor may itself be additive or subtractive of the repolarization waveform. This may result in the further complication of the ability of the sense amplifier to respond shortly after the stimulus is delivered. To offset this problem, various circuits have been devised to provide a fast recharge of the output capacitor, such as the commonly assigned copending U.S. patent application Ser. No. 184,777, filed Sept. 8, 1980, entitled Body Stimulator, and Ser. No. 252,538, filed Apr. 9, 1981 entitled FAST RECHARGE OUTPUT CIRCUIT, now U.S. Pat. No. 4,406,286. The method and apparatus of the present invention is envisaged to operate in conjunction with such Fast Recharge Output Circuits.

In addition, and as a further complication to the design of pacemaker sense amplifier circuits, it may become necessary in atrial and ventricular synchronous pacemaker design to provide a blanking, that is a disconnecting of the input terminals of one or more of the sense amplifiers from the respective lead electrodes, following the delivery of a stimulting pulse on the same or other set of output terminals. For example, in an unipolar atrial synchronous pacemaker, it is necessary to blank the ventricular sense amplifier during the delivery of the stimulus by the atrial output circuit, since the atrial output signal is strong enough, after passing through the heart muscle, to be detected by the ventricular sense amplifier which would register a false sensing of an R wave. It is desirable that the ventricular sense amplifier be blanked for a very short interval so that it may be made ready to sense the ventricular depolarization, if any, triggered by the atrial stimulus after the A-V interval, or any premature ventricular contraction. The sensing of the ventricular depolarization would obviate the necessity of the pulse generator from providing a synchronized ventricular stimulation following the atrial stimulation.

The present invention overcomes the problem arising from polarization voltages present on a lead. In certain cases, the polarization voltage may cause the ventricular sense amplifier to register a false sense signal at the end of the ventricular blanking period, since the reconnection of the ventricular sense amplifier input terminals may itself cause some voltage transients, which, when coupled to a higher slew rate repolarization voltage, be sufficient to trigger the ventricular sense amplifier.

In other cases, the repolarization signals or T wave superimposed on the polarization voltage could have a high enough slew rate to trigger the sense amplifier, causing inappropriate T wave sensing. This can occur with interference signals.

SUMMARY OF THE INVENTION

Figure 1:
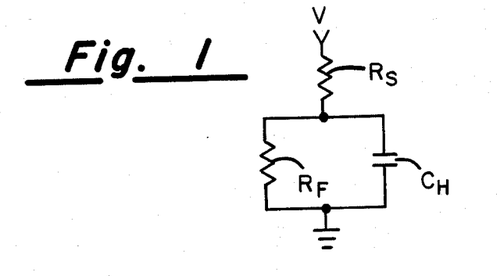
FIG. 1 is an illustrative schematic diagram of the effective electrode-tissue impedance.

According to the present invention there is provided a method and apparatus embodied in a pacemaker for attenuating polarization currents or voltages at the output terminals of the pulse generator. A heart pacemaker of the type contemplated to be employed in the practice of the present invention typically possesses a source of supply voltage, an output capacitor, an output terminal adapted to be coupled to heart tissue. Means are provided for coupling the supply voltage source to the output capacitor during the first time interval for charging the output capacitor to a certain voltage, and further means are provided for coupling the output capacitor to the output terminals during a second time interval to discharge the output capacitor voltage into the heart tissue. In accordance with the present invention, a further impedance means is coupled across the output terminals for providing a current path for the discharging and recharging of the effective capacitance of the stimulated heart tissue electrode interface. The impedance means according to the embodiment of the present invention may comprise a resistor on the order of about 26 K ohms in value, which, when coupled across the reactance depicted in FIG. 1, provides a further discharge circuit for the Helmholtz capacitance $C_H$, thereby altering and in effect flattening the polarization voltage curve A depicted in FIG. 2.

In accordance with a further embodiment of the present invention, it is contemplated that impedance means may be coupled with further switching means for switching impedance means into the circuit only for a short interval after the stimulus and prior to the cell depolarization. In this embodiment, lower impedances can be considered.

In addition, it is contemplated that the method and apparatus of the present invention may be accomplished in conjunction with an atrial and ventricular pacemaker having an atrial sense amplifier, an atrial output circuit, atrial output terminal means coupled thereto and adapted to be coupled by an atrial pacing lead to atrial pacing electrodes in electrical contact with the atrium of the heart, a ventricular sense amplifier and ventricular output circuit coupled to ventricular output terminals which are adapted to be connected by a ventricular pacing lead to ventricular pacing electrodes in electrical contact with the ventricle of the heart, and a digital controller and programmable memory control circuit for controlling the operation of the atrial and ventricular output circuit means in response to sensed atrial and ventricular depolarization of the heart. Blanking circuit means are provided in this embodiment to blank the ventricular sense amplifier during selected intervals. The resistance means is coupled across the output terminals.

The invention is useful in both unipolar and bipolar pacemakers, and particularly useful in unipolar pacemakers, because of cross talk between atrial signals and ventricular signals in the case of unipolar pacemakers. The preferred embodiment shown herein is for a unipolar pacemaker.

The foregoing and additional advantages in characterizing features of the present invention will become clearly apparent upon reading of the ensuing detailed description, illustrative embodiments thereof together with the included drawings depicting the same.

DETAILED DESCRIPTION OF THE PREFERRED EMBODIMENT

As described hereinbefore, the drawing FIGS. 1 and 2 depict representations of the effective impedance of the cardiac tissue and electrode interface and the potentials exhibited by the cardiac tissue during and after recharge of the output capacitor. The high rate of change of the polarization potential presents problems to the sense amplifier input circuits in the event that any noise or cell repolarization or circuit component switching transients occur during the rise time of the polarization potential. The curve A in FIG. 2 represents the polarization voltage seen on terminal 40-30 at the end of the fast recharge when an output stage as described in FIG. 5 as used without amplifier 66 and recharge control logic 68 (that is, a circuit like that shown in the aforementioned U.S. patent application Ser. No. 184,777). The curve B of FIG. 2 shows the effect of the invention on the curve A of FIG. 2.

Figure 3:
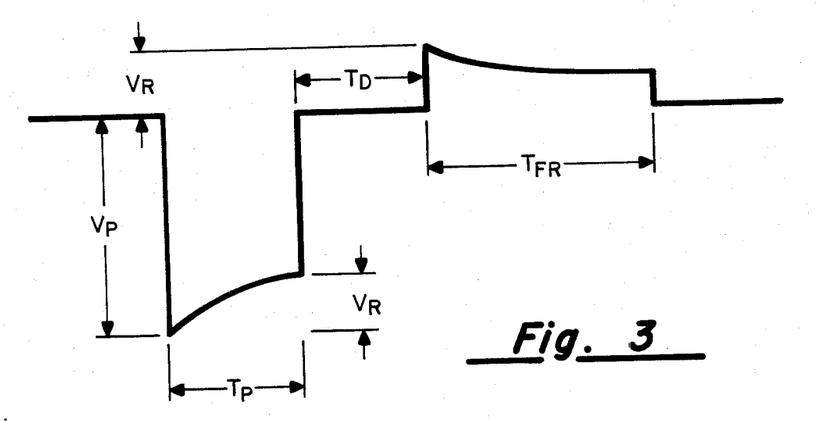
FIG. 3 is a waveform diagram of the stimulating impulse provided by the discharge of an output capacitor and the subsequent fast recharge of the output capacitor of a pacemaker pulse generator.

FIG. 3 depicts a waveform diagram of the stimulating output pulse provided by the discharge of an output capacitor and the subsequent recharge of the output capacitor. The output pulse is a negative pulse which decays (in absolute value) exponentially as a function of the discharge of the output capacitor. The amount that the capacitor discharges is a function of the pulse width $T_P$ and the electrode-heart tissue reactance, and in the illustration is an amount designated as $V_R$. The delay interval $T_D$ is a short interval set by components of the output circuit such as about 0.5 ms. The fast recharge period $T_R$ is set ordinarily at 6-12 ms.

The fast recharge waveform as shown in the drawing would appear at the output terminals as an opposite polarity voltage pulse with an initial nominal amplitude $V_R$ equal to the discharge of the output capacitor (assuming the absence of the voltage stored at that time by the Helmholtz capacitance $C_H$). The voltage of the fast recharge waveform depicted decreases as the output capacitor recharges.

The operation of a fast recharge output circuit of the type described in the aforementioned U.S. Pat. No. 4,406,286 greatly reduces the slew rate voltage during the last part of the cardiac cycle resulting in the line C depicted in FIG. 6. The decaying voltage depicted in waveform C however still exhibits a slew rate during the time in which a sense amplifier may be unblanked. The combination of the switching transients and the slew rate may still cause false triggering under w certain circumstances. In very general terms, the greater the polarization voltage (which may vary from patient to patient and as a result of the surface over and material of pacing electrodes employed and the width of the stimulation pulse), the greater or more prolonged the slew rate of the waveform C of FIG. 6 will be. FIG. 6 will be discussed in greater detail in reference to FIG. 5.

Figure 4:
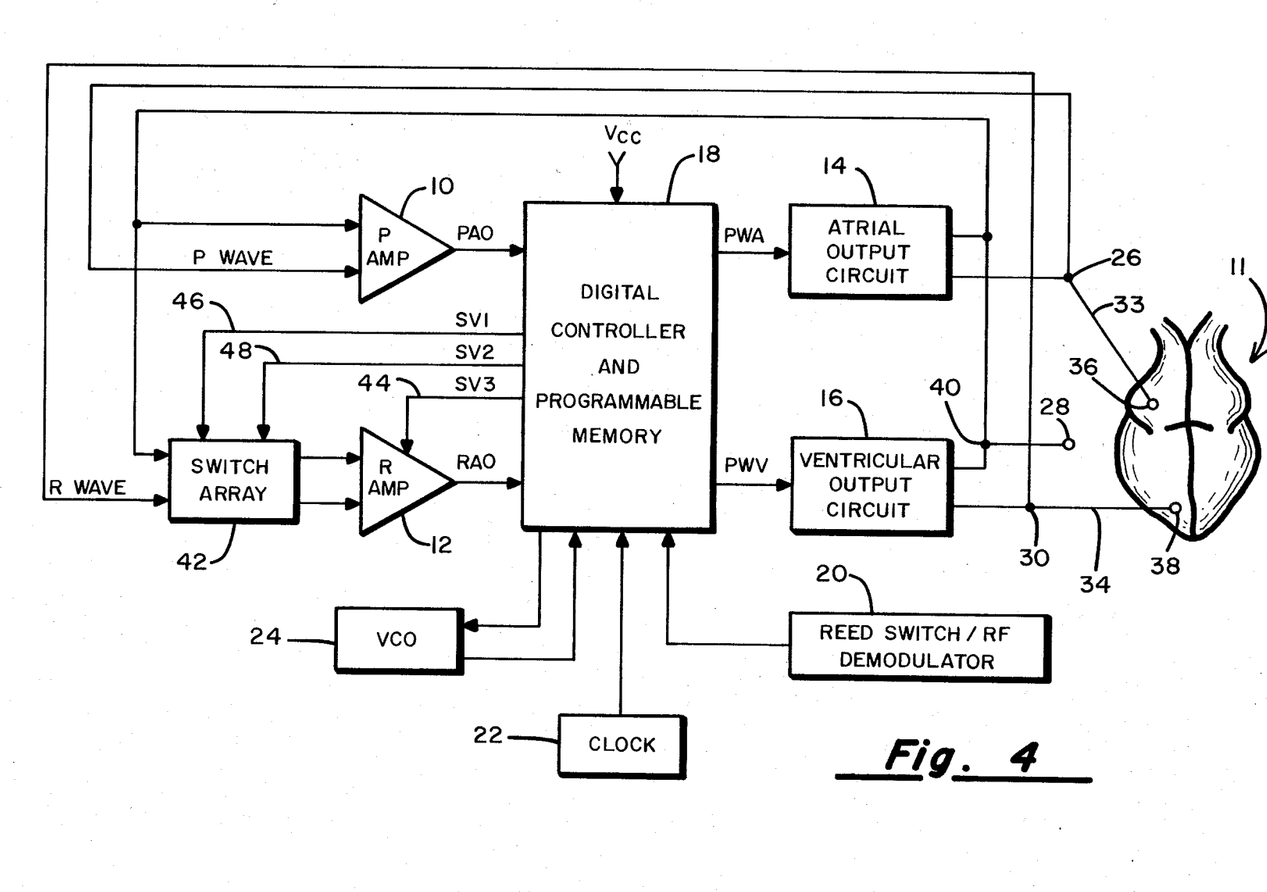
FIG. 4 is a block diagram of a heart pacemaker in which the present invention may be implemented.

In FIG. 4, the major functional elements of a pacemaker in which the present invention can be practiced are shown in block diagram form. The pacemaker could either be external or implantable, but, in either case, it is connected through leads to the patient's heart.

The illustrative dual chamber pacemaker possesses five basic components in addition to the necessary power supply and leads for conducting electrical signals between the patient's heart and the pacemaker pulse generator. These components are an atrial sense amplifier, a ventricular sense amplifier, an atrial output stage, a ventricular output stage, and a digital controller circuit possessing programmable memory and logic circuits which time the production of atrial and/or ventricular stimulating output pulses as a function of the P waves sensed by the atrial sense amplifier, R waves sensed by the ventricular sense amplifier, parameter and mode data stored within the memory, the status of the power source voltage, and the condition of a reed switch which may be effected by an external magnetic field. It is contemplated that, in the preferred embodiment of this invention, the pulse generator would be contained within a sealed metallic container electrically connected to the output stages to act as an indifferent electrode and a pair of output connectors or terminals adapted to be coupled by way of leads from the output terminals extending to the atrium and ventricle of the patient's heart.

It is further contemplated that the dual chamber pacemaker of the present invention may automatically operate in several different pacing modes depending on the presence or absence of sensed atrial and/or ventricular depolarizations, that is P waves and/or R waves, in a manner described generally, for example, in U.S. Pat. No. 4,312,355. In this context, it is contemplated that several modes of operation may automatically take place depending on the condition of the patient's heart.

Generally, if neither P waves nor R waves are present in the atrial and ventricular escape intervals set by the timing circuitry of the pacemaker, it will function in the dual chamber, A-V sequential fixed rate mode (DOO mode as this mode and others referred to herein are designated in the Report of the Inter-Society Commission for Heart Disease Resources in *Circulation*, Vol. L., October, 1974). If P waves are not present, but R waves recur from time to time within the A-V delay interval, the device operates in the A-V sequential demand or DVI mode. If P waves are present, this device operates in the atrial synchronous or VAT mode in the absence of R waves sensed within the A-V escape interval or in the atrial synchronous ventricular inhibited (ASVIP) of VDD mode when R waves recur within the A-V interval.

In addition, it is contemplated that the dual chamber pacemaker of the present invention may be externally programmed to operate in a number of different modes including: the fully automatic dual chamber, or DDD mode described above, in which the atrial and ventricular sense amplifiers and the atrial and ventricular output stages are fully operational; in the atrial-ventricular sequential pacing mode, or DVI mode, wherein atrial and ventricular stimulating pulses are provided in timed relationship to one another in the absence of sensed ventricular depolarization; in the atrial-synchronous, ventricular inhibited (ASVIP) mode, or the VDD mode, wherein the sensed atrial depolarization cause the pulse generator to deliver a ventricular stimulation pulse unless a spontaneous or conducted ventricular depolarization is detected by the ventricular sense amplifier prior to the timing out of a suitable A-V delay period; or the ventricular demand pacing mode, the VVI mode, wherein the atrial sense amplifier and atrial output stages are not employed.

Furthermore, it is contemplated that the pulse generator can be programmed to operate in the atrial synchronous mode (AOO), the ventricular asynchronous mode (VOO), or the atrial and ventricular asynchronous modes (DOO), by selectively programming atrial and/or ventricular pulse widths to zero and sensitivity to infinite to arrive at the resulting combination.

Turning now again to FIG. 4, there is shown an atrial sense amplifier 10, ventricular sense amplifier 12, atrial output stage 14, ventricular output stage 16, digital control and logic circuit 18, and three further circuits, the RF modulator circuit 20 for receiving remotely applied programming signals and magnetic field test signals, a crystal oscillator 22 for providing the basic clock frequency for the digital control and logic circuit 18, and a voltage controlled oscillator (VCO) circuit 24 for timing certain operations of the digital control and logic circuit 18. The atrial sense amplifier 10 is coupled between the atrial lead terminal 26 and the pulse generator 28 for sensing atrial depolarizations or P waves. The ventricular sense amplifier 12 is similarly coupled to the case terminal 28 and the ventricular pacing lead terminal 30, for sensing ventricular depolarizations or R waves. The digital control and logic circuit 18 is coupled to the output terminals of the atrial and ventricular sense amplifiers to receive the atrial amplifier output signal and the ventricular amplifier output signal, to process the signal in accordance with the mode to which the pacemaker is programmed and the parameters of atrial and ventricular timing escape intervals, and to produce, if appropriate, atrial pace initiate signals and ventricular pace initiate signals which are respectively coupled to input terminals of the atrial output stage 14 and the ventricular output stage 16 to initiate respective atrial and ventricular stimulating pulses. The production of the atrial and/or ventricular initiate pulses is dependent upon the presence or absence of sensed atrial and/or ventricular depolarizations of the heart within certain escape intervals established by the parameter data stored in memory within the digital control and logic circuit 18 and dependent upon whether or not the reed switch (circuit 20) is open or closed by the application of an external magnet or on the condition of interference detector (not shown) within the ventricular sense amplifier 12 which responds to noise signals picked up by the ventricular sense amplifier. Ignoring for the moment the possibility of the closure of the reed switch 20 or interference, and turning to the operation of the circuit in the DDD mode, the pulse generator will pace at a programmable lower rate if neither P waves or R waves are sensed within the escape intervals established by lower rate data stored in memory. The A-V interval between the production of atrial and ventricular initiate signals by the digital control and logic circuit 18 is similarly programmable and, under these conditions, the total operation of the pacemaker is characterized as A-V sequential demand pacing.

If a P wave is sensed by the atrial sense amplifier 10 within the programmed atrial escape interval, (corresponding to a programmable lower rate), the digital control and logic circuit 18 will not produce an atrial pace initiate signal, but instead will commence the timing of the A-V interval. If an R wave is sensed by the ventricular sense amplifier 12 prior to the expiration of the A-V interval, the ventricular pacing initiate signal is similarly not produced, and all timing intervals will be reset. But, if an R wave is not sensed prior to the completion of the A-V interval, a ventricular pace initiate pulse will be provided by the digital control and logic circuit to initiate the production of a ventricular pacing stimulus at the end of the delay.

If the memory within the digital control and logic circuit 18 is programmed to the VVI mode, the atrial sense amplifier output signal is ignored, and the atrial output initiate signal is not produced. Thus, the digital control and logic circuit 18 responds only to R waves sensed by the venticular amplifier 12 and produces only ventricular pace initiate signals in the absence of an R wave occurring prior to the expiration of the ventricular escape interval.

If the device is programmed in the DVI mode, the atrial output signal of the atrial sense amplifier 10 is similarly ignored. However, the atrial output stage and the ventricular output stage receive atrial and ventricular pace initiate signals at the programmable lower rate and separated by the A-V interval. If an R wave is sensed during the escape interval and following the refractory period of the ventricular sense amplifier, the lower rate timing is reset. If an R wave is sensed prior to the completion of the A-V interval and following the delivery of an atrial stimulating pulse to the heart, then the ventricular pace initiate signal is inhibited or not delivered and the lower rate escape interval is again reset.

In the atrial synchronous ventricular inhibited, or VDD mode, P waves recurring at a rate exceeding the programmable lower rate, are sensed by the atrial sense amplifier and processed by the digital control and logic circuit 18 to commence the A-V timing interval. Again, if an R wave is sensed prior to the completion of the A-V interval, the ventricular pacing output is inhibited and all timing circuits will be reset. But, if an R wave is not sensed prior to the completion of the A-V interval, a ventricular pacing stimulus will be provided in response to a ventricular pace initiate signal at the end of the A-V interval. A sensed R wave occurring within the programmed lower rate escape interval and after the refractory period since the last ventricular depolarizatin or stimulating pulse, will be processed by the digital control and logic circuit 18 to restart the lower rate timing interval.

The above modes of operation may be selected by the physician to conform the operation of the pacemaker to the patient's condition or the condition of the atrial or ventricular pacing leads. Ordinarily it would be expected that the pacemaker would be left operating in the fully automatic dual chamber or DDD mode, with the lower rate interval, A-V timing interval and other parameters of the operation of the device being selected and programmed to conform to the patient's condition.

FIG. 4 also indicates a diagrammatic representation of the patient's heart. A lead 33 extends to the atrium or upper chamber of the heart, and lead 33 has an electrode 36 which contacts the heart at the atrium. Similarly, lead 34 extends to the ventricle or lower chamber of the heart, and it has an electrode 38 at its end which contacts the heart at the ventricle. Although two separate leads 33 and 34 are shown, a single multiple conductor lead having separate electrodes at its tip and at a point along its side may be used for contact with the ventricle and atrium, as is generally known in the art. Leads 33 and 34 connect respectively to terminals 26 and 30 provided on the connector of the pulse generator for connection to the various electrical components and circuits within the pulse generator. An indifferent electrode 28, which may be the pulse generator case, is connected to terminal 40 and the various circuits shown in FIG. 4.

Finally in respect to FIG. 4, the R wave amplifier 12 is coupled to the switch array 42 into the digital controller and programmable memory 18 through lines 44, 46 and 48 in such a fashion that the ventricular sensing channel of the pulse generator is disconnected from the terminals 28 and 30 for a short interval (or "blanked") during and following the delivery of an atrial stimulating pulse to the terminals 26 and 28 by signal SV1 and the gain of the amplifier 12 is reduced for a shorter interval by signal SV2. In addition, the signal SV3 is applied to the ventricular amplifier 12 to disable its output for a predetermined time interval following the delivery to the digital controller and programmable memory 18 of the last ventricular sense signal RA0 developed by the ventricular amplifier 12. During this interval, the input terminals of the ventricular amplifier 12 are coupled to the terminals 28 and 30, but any signal which is sensed as an R wave cannot be delivered to the circuit 18. The time duration of the signal SV2 is selected to be somewhat shorter than the ordinary ventricular blanking interval.

Figure 5:
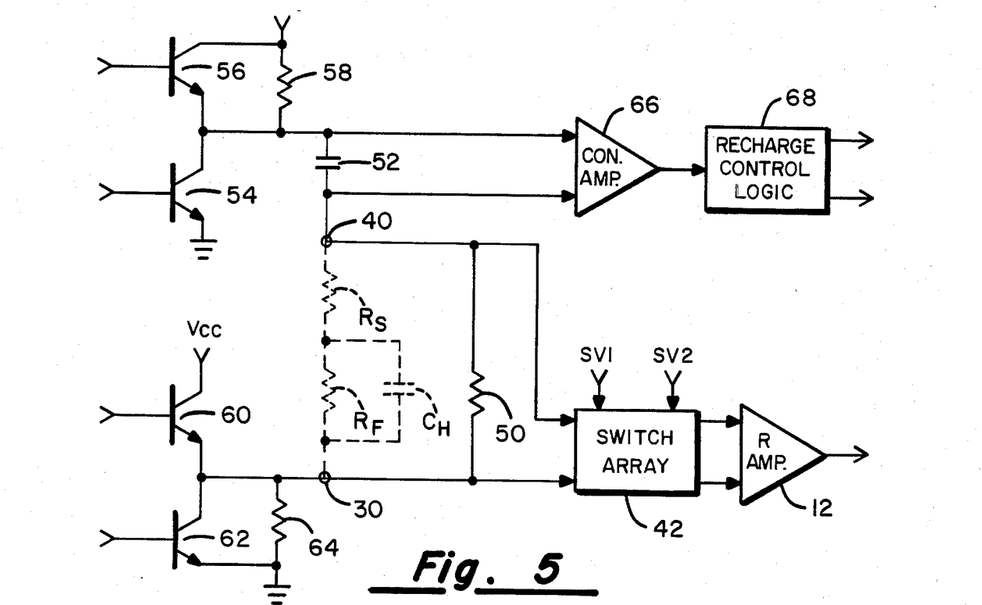
FIG. 5 is a circuit diagram of a preferred embodiment of the circuit for reducing the effects of polarization potentials of the present invention.
Figure 6:
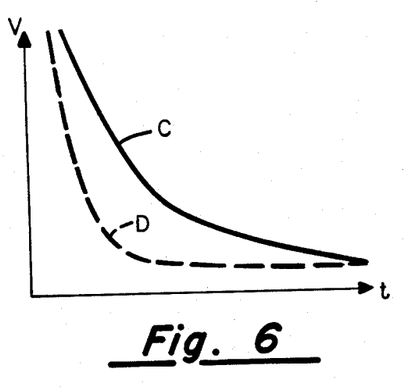
FIG. 6 is a waveform diagram of the improved aggregate slew rate of the voltage potential after automatic fast recharge of the output capacitor as seen at the output terminals of the circuit of FIG. 4.

Turning now to FIG. 5, there is depicted a simplified circuit diagram of the fast recharge output circuit of the type described more explicitly in the aforementioned U.S. Pat. No. 4,406,286 and a preferred embodiment of the present invention for reducing the repolarization voltage slew rate exhibited at the output terminals. In FIG. 5, the cardiac tissue reactance is depicted in broken lines by the components $R_S$, $R_F$ and $C_H$ (described above in reference to FIG. 1) coupled across the output terminals 30 and 40. The output terminals 30 and 40 in this embodiment are presumed to be the output terminals of the ventricular output circuit 16 (which would contain certain of the remaining components depicted in FIG. 5) and are coupled via the switch array 42 to the ventricular sense amplifier 12. The output terminal 40 is also coupled to one side of the output capacitor 52, the other side of which is coupled to the collector of the discharge transistor 54, the emitter of the fast recharge transistor 56 and the load resistor 58. The transistors 54 and 56 and the resistor 58 are arranged across the source of supply voltage $V_{cc}$ and ground potential. The output terminal 30 is coupled to the emitter of the second discharge transistor 60 and the collector of the second fast recharge transistor 62 and the second load resistor 64. The capacitor 52 is also coupled to the input terminals of a control amp 66. The output of the control amplifier 66 is applied to control logic 68 for controlling the fast recharge of the output capacitor 52.

A complete description of the operation of the control amp 66 and control logic 68 to operate the fast recharge of the output circuit depicted in FIG. 5 may be found in the aforementioned U.S. Pat. No. 4,406,286. In very general terms, the output capacitor 52 is charged by the voltage source $V_{cc}$ when the transistors 56 and 62 are rendered conductive during the fast recharge interval $T_{FR}$. The fast recharge takes place through the conductive path established by the transistor 56, capacitor 52, the tissue reactance between the output terminals 30 and 40 and the transistor 62. The level to which the output capacitor 52 is recharged is controlled by differential circuit included in the control amp 66 which triggers the control logic 68 to control the conduction of the transistors 56 and 62. After the fast recharge interval, the charge on capacitor 52 is maintained through trickle currents passing through the load resistors 58 and 64 and the tissue impedance.

The output capacitor 52 is discharged into the tissue reactance by rendering transistors 54 and 60 conductive in a manner described in the aforementioned U.S. Pat. No. 4,406,286 for the interval $T_P$. When discharge takes place, the voltage $V_{cc}$ and the voltage on capacitor 52 are additively applied to the tissue reactance. At the end of the interval $T_P$, the control logic 68 provides the interval $T_D$ which precedes the fast recharge interval $T_{FR}$. In reference to FIG. 4, the ventricular pace initiate signal PWV would indirectly be applied to the base terminals of transistors 54 and 60 for the interval $T_P$, and logic circuit 68 would provide the recharge signal to the base terminals of transistors 56 and 62.

In addition, the sense amplifier 12 is coupled across the output terminals 30 and 40. The sense amplifier 12 may be blanked by the opening of FET switches (not shown) in switch array 42 for a time interval of about 8–12 ms which commences at an instant just preceding the discharge interval $T_P$ of the output capacitor of the atrial output circuit 14 (not shown). Simultaneously with the opening of the switch array, it may be advantageous to reduce the gain of the ventricular sense amplifier 12. The gain of the ventricular sense amplifier 12 may be restored about 4 ms. after the reconnection of the sense amplifier terminals to the output terminals 30, 40 to reduce the possibility of switching transients providing a false sense indication. The blanking of the sense amplifier 12 is controlled in a fashion described more fully in commonly assigned copending U.S. patent application Ser. No. 235,069 filed Feb. 17, 1981, and entitled Implantable Medical Device Power Source Depletion Indicator, now U.S. Pat. No. 4,390,020.

The operation of the circuitry of FIG. 5 has been described in conjunction with the aforementioned U.S. Pat. Nos. 4,390,020 and 4,406,286 which describe an atrial and ventricular pacemaker pulse generator which is embodied commercially in the Medtronic Versatrax TM Model 7000 series pulse generators.

Turning now to the present invention, applicant has realized that while considerable emphasis has been placed in improving sense amplifier design and in effecting fast recharge or biphasic output circuits, a significant improvement in the operation of the pulse generator can be obtained by instead altering the effective reactance of the heart as viewed from the pulse generator output terminals. To that end, applicant has added a resistor 50 across the output terminals 30 and 40 (FIG. 4) which modifies the effective impedance or reactance of the tissue and furthermore provides a further discharge current path for the Helmholtz capacitance $C_H$. Applicant has found that resistor 50 on the order of about 25 Kohms is optimal for use with the circuit components employed in the aforementioned Medtronic Versatrax TM pulse generator. Applicant has also found that the resistor 50 becomes less effective as a discharge path as the resistance is increased above 25 Kohms and negatively affects the sense amplifier performance as resistance is reduced below 25 Kohms particularly below about 15 Kohms. Thus, the resistance of about 25 Kohms is optimal for the Versatrax TM pulse generator.

The effect of the discharge current path provided by resistor 50 is depicted in FIG. 6, when using an output stage as described in FIG. 5 with circuit 66 and 68 working (when circuits 66 and 68 are inactive, FIG. 2 applies). In FIG. 6, waveform C is in effect simply the decay without the parallel impedance 50 of the polarization voltage stored in the Helmholtz capacitor $C_H$ as seen at the sense amplifier input terminals. The waveform D of FIG. 6 is the decay of the polarization voltage with the additional impedance 50 in the circuit. As can be seen the waveform C presents a declining slew rate over time which may extend to the end of the SV3 intervals, whereupon the switching transients upon closure of the FET switches in switch array 42 could trigger a false sense output RAO. The waveform D is a decaying voltage with a shorter time constant, that is it rapidly changes early during the first part of the SV3 time interval, and susequently the rate of change of the voltage seen at the input terminals of the sense amplifier 12 is very low. In this case, the parallel impedance to the heart tissue interface, that is, the resistor 50, helps to more rapidly discharge the Helmholtz capacitor $C_H$. The voltage seen by the sense amplifier 12 is a decaying voltage with a shorter time constant than the voltage exhibited by waveform C of FIG. 6.

Figure 7:
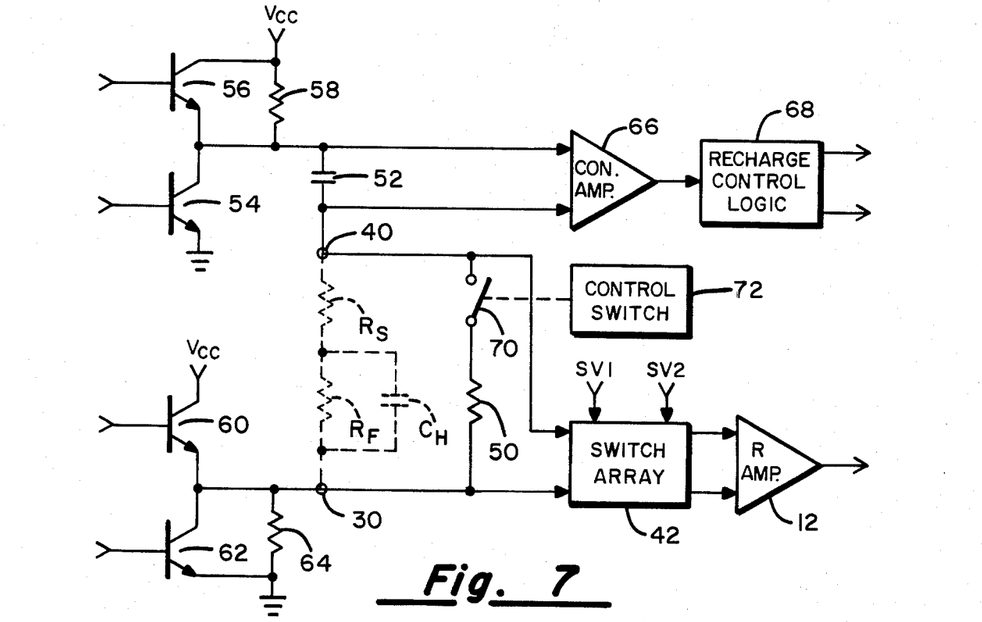
FIG. 7 is a further circuit diagram in part of a further embodiment of the circuit of the present invention.

Turning now to FIG. 7, there is shown a circuit similar to FIG. 5, that is, the output terminals 30 and 40, and the resistor 50 with an additional switch 70 which may be controlled by the control logic 72. In this embodiment it is contemplated that the switch 70 would be closed after the recharge interval $T_{FR}$ to load the heart tissue reactance with the resistor 50 and to discharge the polarization potential as described above.

One could decay the polarization voltage in extremely short time (10–20 ms). After the decay of the polarization voltage, one could increase the sensitivity of the sense amplifier 12, and so be able to detect the QRS complex following a ventricular stimulation by way of the sense amplifier 12. The detection of the induced electrical activity of the heart is normally called "capture detection."

The switch 70 would be reopened after a suitable time interval so that the heart impedance as viewed at the output terminals 30 and 40 by the sense amplifier 12 would not be modified during the major portion of the escape interval of the pulse generator. In this embodiment, a lower impedance than the suggested 25 Kohms may be employed to discharge the polarization voltage even quicker while the sense amplifier sensitivity would not be impaired by the lower impedance (which would, when present, attenuate the amplitude of the heart's own ECG) during the major portion of the escape interval between successive output pulses of the pulse generator.

While the impedance 50 has been depicted as a resistor, an inductor could possibly by employed as well. In case one would like to prolong the effect of the polarization voltage (just the opposite is described above) one could substitute a capacitor for the resistor 50 or a combination of inductors and capacitors. The invention may also be implemented in any suitable analog or digital circuitry including software controlled custom or conventional microprocessors. These and other modifications or uses of the invention will be apparent to those skilled in the art.

I claim:

1. In a heart stimulator having a source of supply voltage, timing circuit means for providing first and second time intervals, a pair of output electrodes for applying a stimulating pulse to heart tissue, and an output capacitor coupled to one of said output electrodes, the improvement for attenuating polarization currents/-voltages at said output electrodes comprising:

first means for coupling said supply voltage source to said output capacitor during said first time interval for charging said output capacitor to a certain voltage;

second means for coupling said output capacitor to both of said output terminals during said second time interval to discharge said output capacitor voltage into, and thereby stimulate heart tissue; and resistor means coupled across said output electrodes for providing a current path for the discharging of the effective capacitance of previously stimulated heart tissue and the charging of said output capacitor during said first time interval, said resistor means having a resistance sufficiently low to discharge said effective capacitance.

2. The heart stimulator of claim 1 further comprising:

sense amplifier means having input terminals coupled across said output terminals and said resistor means for sensing electrocardiograms of the heart due to spontaneous and evoked depolarization of heart tissue.

3. The heart stimulator of claim 2 further comprising:

blanking circuit means for decoupling said sense amplifier input terminals from said output terminals during said second time interval, said delay interval and said fast recharge interval.

4. The heart stimulator of claims 1, 2 or 3 wherein said first means further comprises:

charging impedance means connected in the circuit with said supply voltage source and said output capacitor for applying charging current to said output capacitor regulated by the impedance of said charging impedance means;

further timing circuit means for providing a delay interval during said first time interval and following said second time interval;

fast recharge switching means coupled across said charging impedance means; and recharge control logic means responsive to said further timing circuit means and the state of charge of said output capacitor for selectively closing said charging switching means and providing a fast recharge of said output capacitor during a fast recharge time interval following the discharge of said output capacitor and said delay time interval.

5. The heart stimulator of claim 4 further comprising:

switching means for periodically coupling and decoupling said resistor means across said output electrodes during said first time interval and after said fast recharge interval.

6. An atrial and ventricular cardiac pacemaker pulse generator comprising:

a source of supply voltage;

atrial and ventricular output terminals adapted to be electrically coupled through respective atrial and ventricular pacing leads and electrodes to make electrical contact with atrial and ventricular heart tissue, respectively;

atrial and ventricular timing circuit means for providing first and second time intervals;

atrial and ventricular output circuits coupled to said output terminals and said timing circuit means, each respective output circuit further comprising:

an output capacitor coupled to one of said output terminals;

first means for coupling said supply voltage source to said output capacitor during said first time interval for charging said output capacitor to a certain voltage; and second means for coupling said output capacitor to both of said output terminals during said second time interval to discharge said output capacitor voltage into, and thereby stimulate, heart tissue;

resistor means coupled across said output terminals of said ventricular output circuit for providing a current path for the discharging of the effective capacitance of previously stimulated heart tissue and the charging of the ventricular output capacitor during said first time interval, said resistor means having a resistance sufficiently low to discharge said effective capacitance; and control circuit means for controlling the synchronized application of said first and second time intervals to said atrial and ventricular output circuits.

7. The heart stimulator of claim 6 further comprising:

ventricular sense amplifier means having input terminals coupled across said ventricular output terminals and said resistor means for sensing electrocardiograms of the heart due to spontaneous and evoked depolarizations of heart tissue.

8. The heart stimulator of claim 7 further comprising:

blanking circuit means for decoupling said ventricular sense amplifier input terminals from said ventricular output terminals during said second time interval, said delay interval and said fast recharge time interval.

9. The heart stimulator of claim 8 wherein said control circuit means further comprises:

timing means for timing a pacing escape interval and for providing synchronous atrial and ventricular pace initiate signals at the end of the pacing escape interval;

means responsive to said ventricular sense amplifier for resetting said timing means and restarting said pacing escape interval when a spontaneous depolarization of the heart is sensed by said ventricular sense amplifier; and means for applying said atrial and ventricular pace inititate signals to said atrial and ventricular output circuits;

and wherein said second means of said atrial and ventricular output circuits are responsive to said respective atrial and ventricular pace initiate signals.

10. The heart stimulator of claim 9 further comprising:

atrial sense amplifier means having input terminals coupled across said atrial output terminals for sensing electrocardiograms of the heart due to spontaneous and evoked depolarizations of heart tissue.

11. The heart stimulator of claim 6, 7, 8, 10 or 9 wherein said first means of said ventricular output circuit further comprises:

further timing circuit means for providing a delay time interval during said first time interval and following said second time interval;

charging impedance means connected in the circuit with said supply voltage source and said ventricular output capacitor for applying charging current to said ventricular output capacitor regulated by the impedance of said charging impedance means;

fast recharge switching means coupled across said charging impedance means; and recharge control logic means responsive to said further timing circuit means and the state of charge of said ventricular output capacitor for selectively closing said charging switching means and providing a fast recharge of said ventricular output capacitor during a fast recharge time interval following the discharge of said ventricular output capacitor and said delay time interval.

12. The heart stimulator of claim 11 further comprising:

switching means for periodically coupling and decoupling said resistor means across said ventricular output terminals during said first time interval and after said fast recharge interval.

13. An atrial and ventricular cardiac pacemaker pulse generator comprising:

a source of supply voltage;

atrial and ventricular output terminals adapted to be electrically coupled through respective atrial and ventricular pacing leads and electrodes to make electrical contact with atrial and ventricular heart tissue, respectively;

ventricular sense amplifier means having input terminals coupled across said ventricular output terminals for sensing electrocardiograms of the heart due to spontaneous and evoked depolarizations of the heart;

atrial and ventricular timing circuit means for providing first and second time intervals;

atrial and ventricular output circuits coupled to said output terminals, each respective output circuit further comprising:

an output capacitor coupled to one of said output terminals;

first means for coupling said supply voltage source to said output capacitor during said first time interval for charging said output capacitor to a certain voltage; and second means for coupling said output capacitor to both of said output terminals during said second time interval to discharge said output capacitor voltage into, and thereby stimulate, heart tissue;

resistor means coupled across said output terminals of said ventricular output circuit for providing a current path for the discharging of the effective capacitance of previously stimulated heart tissue, said resistor means having a resistance sufficiently low to discharge said effective capacitance and sufficiently high to maintain satisfactory sensing by said ventricular sense amplifier means; and control circuit means for controlling the synchronized application of said first and second time intervals to said atrial and ventricular output circuits.

14. The heart stimulator of claim 13 wherein said first means of said ventricular output circuit further comprises:

further timing circuit means for providing a delay time interval during said first time interval and following said second time interval;

charging impedance means connected in the circuit with said supply voltage source and said ventricular output capacitor for applying charging current to said ventricular output capacitor regulated by the impedance of said charging impedance means;

fast recharge switching means coupled across said charging impedance means; and recharge control logic means responsive to said further timing circuit means and the state of charge of said ventricular output capacitor for selectively closing said charging switching means and providing a fast recharge of said ventricular output capacitor during a fast recharge time interval following the discharge of said ventricular output capacitor and said delay time interval.

15. The heart stimulator of claim 14 further comprising:

blanking circuit means for decoupling said ventricular sense amplifier input terminals from said ventricular output terminals during said second time interval, said delay interval and said fast recharge time interval.

16. The heart stimulator of claim 13 further comprising:

switching means for periodically coupling and decoupling said resistor means across said output terminals during predetermined portions of said first time interval.

* * * * *